US00PP35171P2

(12) United States Plant Patent
Haddad

(10) Patent No.: US PP35,171 P2
(45) Date of Patent: May 16, 2023

(54) ***CANNABIS* PLANT NAMED 'SW0'**

(50) Latin Name: *Cannabis sativa*
Varietal Denomination: SW0

(71) Applicant: MH Consulting, LLC, Longmont, CO (US)

(72) Inventor: Matthew Haddad, Longmont, CO (US)

(73) Assignee: MH Consulting, LLC, Longmont, CO (US)

( * ) Notice: Subject to any disclaimer, the term of this patent is extended or adjusted under 35 U.S.C. 154(b) by 0 days.

(21) Appl. No.: 17/300,819

(22) Filed: Nov. 17, 2021

(51) Int. Cl.
*A01H 5/02* (2018.01)
*A01H 6/28* (2018.01)

(52) U.S. Cl.
USPC ..... Plt./258

(58) Field of Classification Search
USPC ..... Plt./258
See application file for complete search history.

(56) References Cited

U.S. PATENT DOCUMENTS

PP32,318 P3 * 10/2020 Hand ..... A01H 6/28 Plt./258
PP32,725 P2 * 1/2021 Llosá Llácer ..... A01H 6/28 Plt./258

* cited by examiner

*Primary Examiner* — Susan McCormick Ewoldt
(74) *Attorney, Agent, or Firm* — Plant & Planet Law Firm

(57) ABSTRACT

The unique annual herbaceous *Cannabis* plant variety 'SW0' is provided. The variety can be distinguished by its outstanding features.

7 Drawing Sheets

Latin name of the genus and species:
Genus—*Cannabis*.
Species—*sativa*.
Variety denomination: The new *Cannabis* plant claimed is of the variety denominated 'SW0'.

CROSS REFERENCE TO RELATED APPLICATIONS

None.

BACKGROUND OF THE INVENTION

Field of the Invention

The present invention relates to a new and distinct annual variety of *C. sativa*, which has been given the variety denomination of 'SW0'. 'SW0' is intended for use as for sale in *Cannabis* dispensaries and to make products containing no THC.

Background of the Related Art

The genus *Cannabis* has been in use by humans for millennia, due to the multiplicity of its benefits to humans, including the considerable value and utility of its fiber, the nutritional value of its seeds, and the medicinal value of its floral parts and products made from them. Currently the genus is under intense legal commercialization in the United States as industrial hemp for a variety of purposes including biodegradable plastics and building materials, clothing, paper, food, fuel, and medicines.

Cannabidiol (CBD) extracted from *Cannabis* is widely used in over-the-counter medicines and topical treatments and is also the active ingredient in the FDA-approved drug Epidiolex. CBD is just one of at least dozens—perhaps hundreds—of cannabinoids endogenous to *Cannabis*, tetrahydrocannabinol (THC) being the other cannabinoid that is most well-known. The cannabinoids as a group interact with the human endocannabinoid receptors, which are distributed in the brain and throughout the body. The study of the endocannabinoid system (ECS) in humans and other mammals is an area of increasing interest and holds tremendous promise for the future of medicine. See, e.g., Russo (2019). *Cannabis* and Pain, *Pain Medicine,* 20(10): 1093/pm/pnz227; and Russo (2016). Clinical Endocannabinoid Deficiency Reconsidered: Current Research Supports the Theory in Migraine, Fibromyalgia, Irritable Bowel, and Other Treatment-Resistant Syndromes, *Cannabis Cannabinoid Res.* 1(1): 154-165.

Typically, marijuana products are available to users for purchase in specialized "dispensaries" that offer dried flower, edibles, tinctures, extracts, and the like. In some cases, a unique or unusual chemical profile, or chemotype, is attractive not only for flower sales but also for use in the preparation of extracts and/or isolates and for the manufacture of a variety of products that possess characteristics of the chemotype.

SUMMARY OF THE INVENTION

The present invention relates to a new and distinct annual variety of *C. sativa*, which has been given the variety denomination of 'SW0'.

The new *C. sativa* variety is a selection resulting from conventional breeding as shown in FIG. 1, followed by genetic modification. At the first step of this breeding, *C. sativa* varieties known as 'Cherry Wine' (unpatented) and 'The Wife' (unpatented), were reciprocally crossed, such that each variety was the seed parent in one cross and the pollen parent in a different cross. Segregating progeny of the reciprocal crosses were selected based upon the phenotypic traits described herein, and particularly those by which the variety 'Superwoman' differs from 'Cherry Wine' and 'The Wife'. At the second step of the breeding, a pollen parent was selected from the cross in which 'The Wife' was the prior pollen parent, and various seed parents were selected from the cross in which 'The Wife' was the prior seed parent. These seed parents were crossed with the pollen parent, as shown in FIG. 1. In the third step of breeding, offspring from the second step were selected based upon phenotypic characteristics described hereof, and the final selection was designated 'Superwoman'. 'Superwoman', which is distinguishable from both 'Cherry Wine' and 'The Wife' as described hereof was then modified using guided RNAi to create a THC-null variant, designated 'SW0', showing reduced expression of THCA synthase. This new variety 'SW0' is substantially indistinguishable in all respects from 'Superwoman' except that 'SW0' is THC-null (meaning no THC is produced in the flower), due to the action of the RNAi construct.

The 'Superwoman' selection was subsequently evaluated for a number of years at Colorado, USA. 'SW0' was selected to be as nearly identical to 'Superwoman' as was attainable. 'SW0' looks the same as 'Superwoman' and further propagation via cloning and meristem tissue culture has shown the same characteristics: the two varieties are meaningfully distinguishable only on the basis of their accumulation of THCA and other forms of THC.

Asexual reproduction of 'Superwoman' by cutting propagation since 2017 at Colorado, USA has demonstrated that it reproduces true to type with all of the characteristics, as herein described, firmly fixed and retained through successive generations of such asexual propagation. Further, asexual reproduction of 'SW0' at Longmont, Colo., conducted in 2021 and 2022, using vegetative cloning and tissue culture has shown essentially identical behavior. A stable seed line of 'Superwoman' was developed by successive generations of interbreeding and selection to correspond to the phenotypic characteristics described herein.

The following characteristics of the new variety have been repeatedly observed and can be used to distinguish 'SW0' as a new and distinct variety of *C. sativa* plant: the new *C. sativa* variety is THC-null.

Plants of the new variety differ from plants of the related variety 'Cherry Wine' (not patented) primarily in tighter internodal spacing, shorter plants, more balanced hybrid, and more balanced CBD ratio. Plants of the new variety differ from plants of the related variety 'The Wife' (not patented) primarily in displaying great resiliency to mold and pathogens, better yields, more vigor, and being more versatile in different growing environments. Plants of the new variety 'SW0' differ from 'Superwoman' (not patented) in having little to no THC % present in mature flowers, while 'Superwoman' has THC levels that exceed the federal 0.3% threshold.

BRIEF DESCRIPTION OF THE DRAWINGS

The accompanying photographic illustrations show the typical appearance of the new variety 'SW0'. The colors are as nearly true as is reasonably possible in a color representation of this type. Colors in the photographs may differ slightly from the color values cited in the detailed botanical description which accurately describes the colors of the new plant.

DETAILED BOTANICAL DESCRIPTION

The following detailed description sets forth the distinctive characteristics of 'SW0'. The data which define these characteristics were collected from asexual reproductions of the original selection, 'Superwoman' which is identical to 'SW0' in all respects except the RNAi construct and the resulting THC-null phenotype. The purpose of this new variety 'SW0' is not a morphological distinction from 'Superwoman' but is a chemovar with no THC. Dimensions, sizes, colors, and other characteristics are approximations and averages set forth as accurately as possible. The descriptions relate to plants grown in Colorado, USA. Color notations are in reference to the standard RGB color chart known to those of ordinary skill in internet website design. Color coordinates were derived using a digital device. In some cases, there is no standard corresponding color name so only the RGB coordinates are provided.

Type: Herbaceous tap-rooted annual.

Classification:

a. *Family*.—Cannabaceae.
b. *Genus*.—*Cannabis*.
c. *Species*.—*sativa*.
d. *Common name*.—Hemp.

Figure 1:
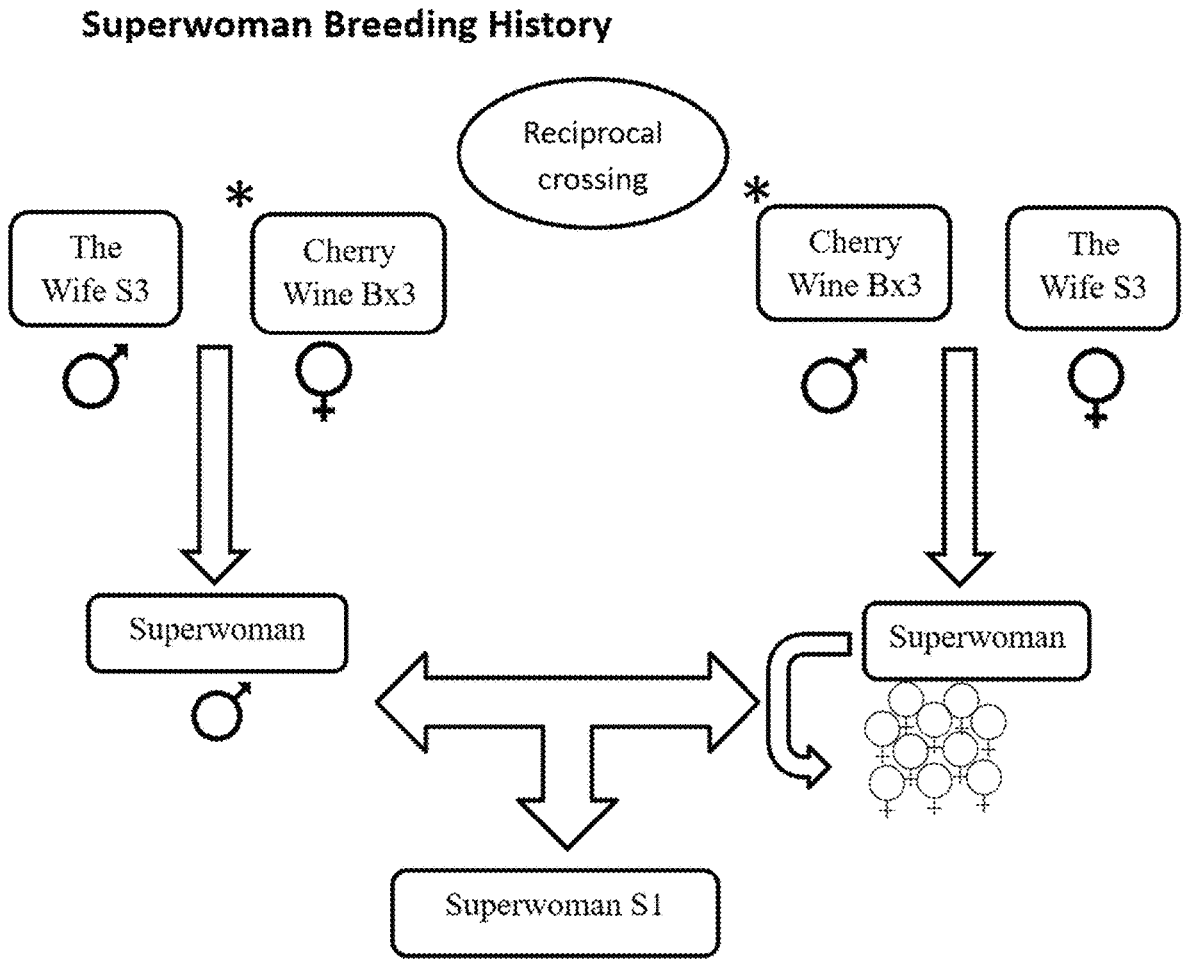
FIG. 1 is a diagram of the breeding history of the 'Superwoman' and the new variety 'SW0'.
Figure 2:
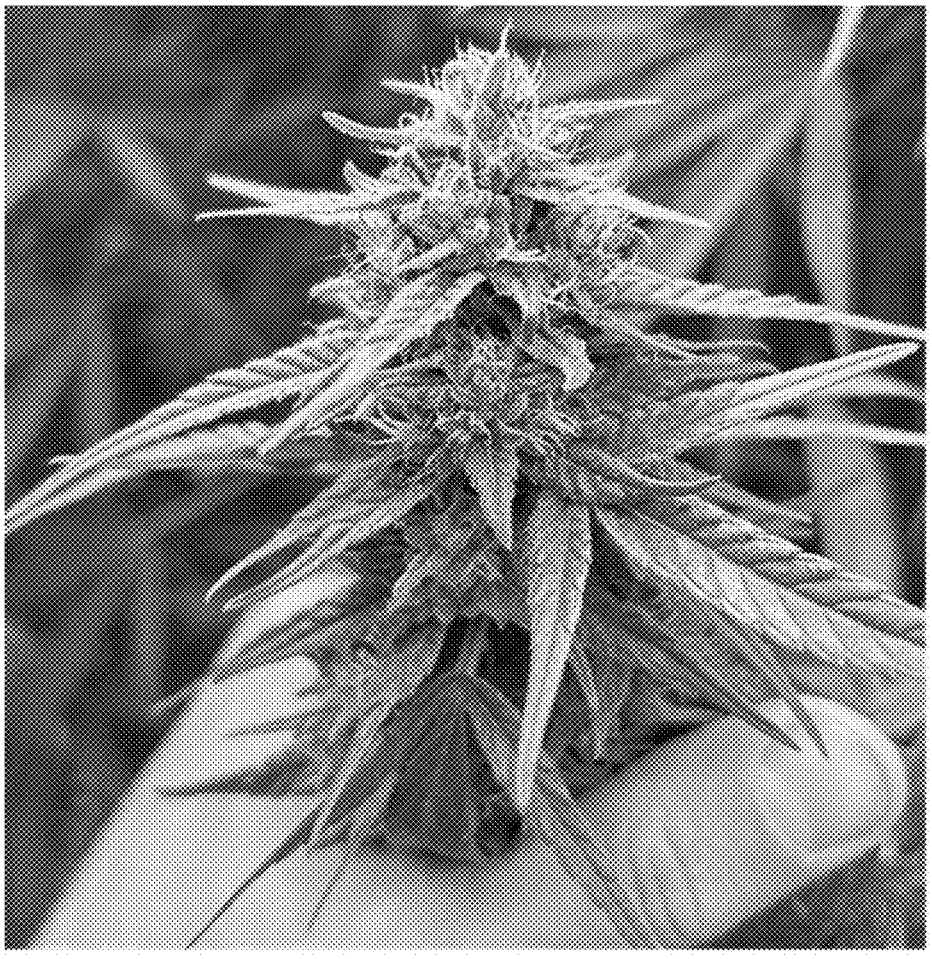
FIG. 2 is a photograph of the flower of a mature 'SW0' plant.
Figure 3:
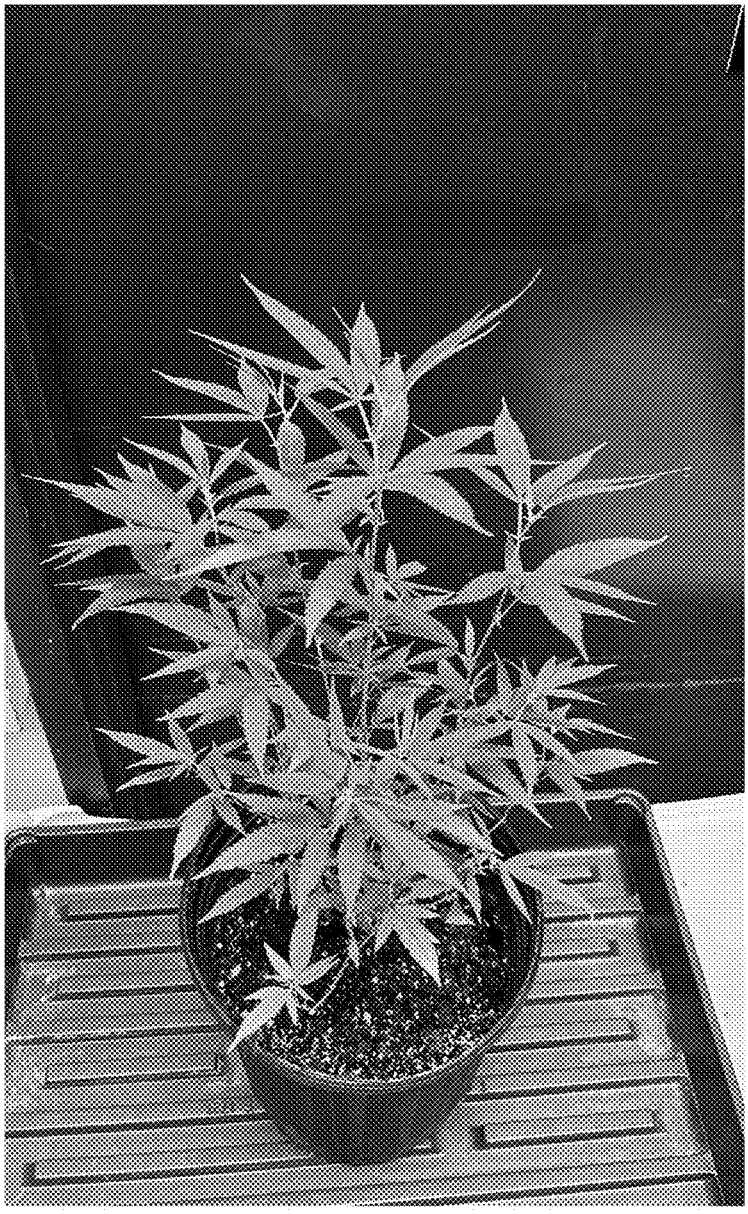
FIG. 3 is a photograph of the whole plant of 'SW0' at 7-8 weeks of age coming out of in-vitro transplant shock to soil.
Figure 4:
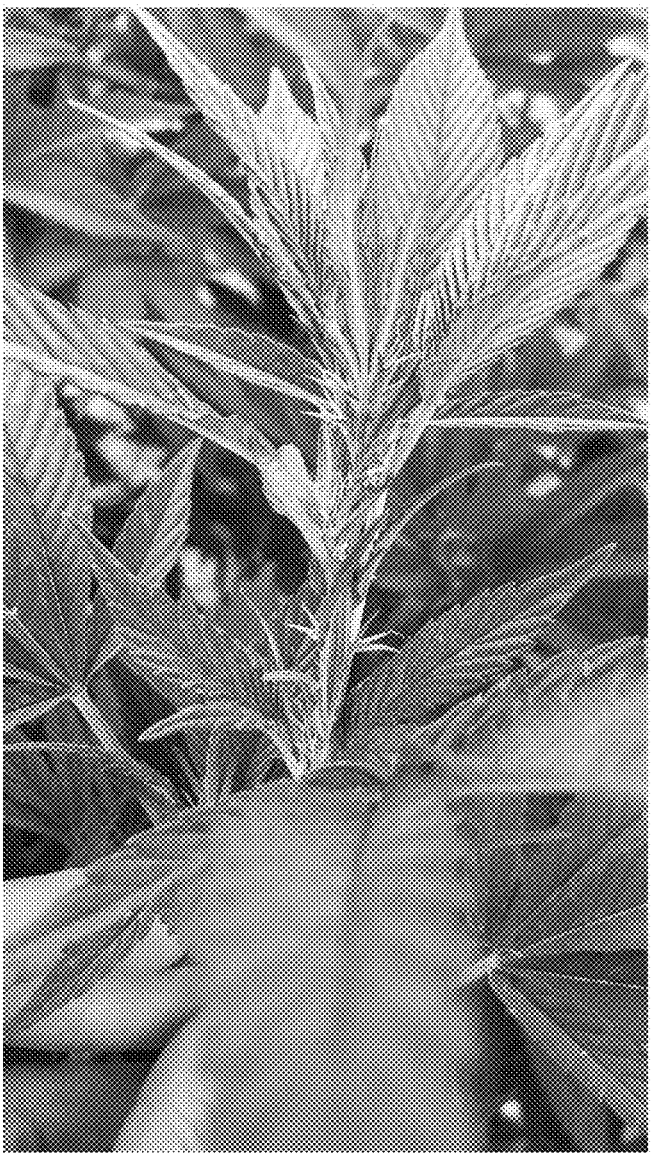
FIG. 4 is a photograph that shows the early stages of a flowering plant of 'SW0'.
Figure 5:
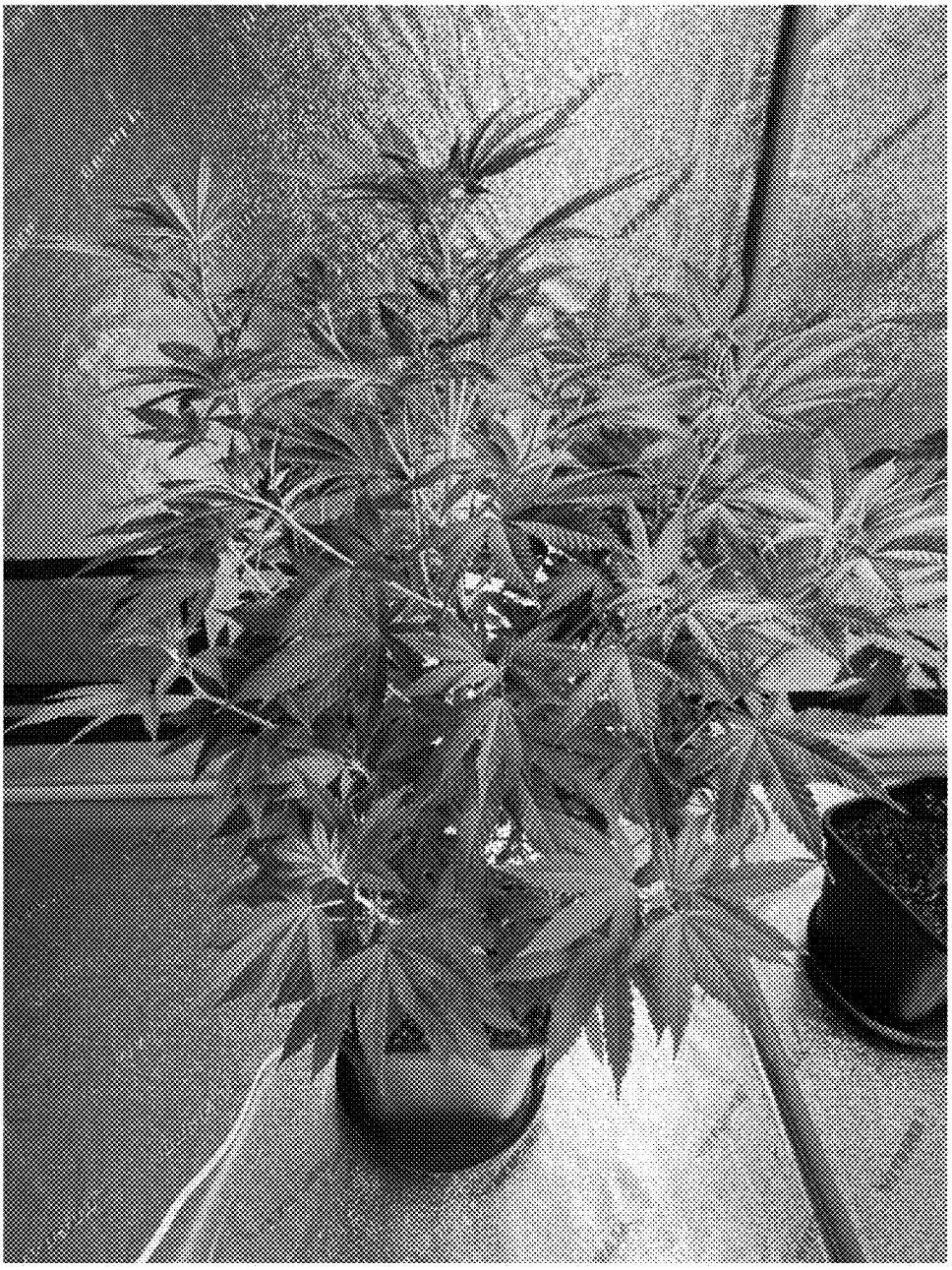
FIG. 5 is a photograph of a healthy 'SW0' plant before going into the flower stage.
Figure 6:
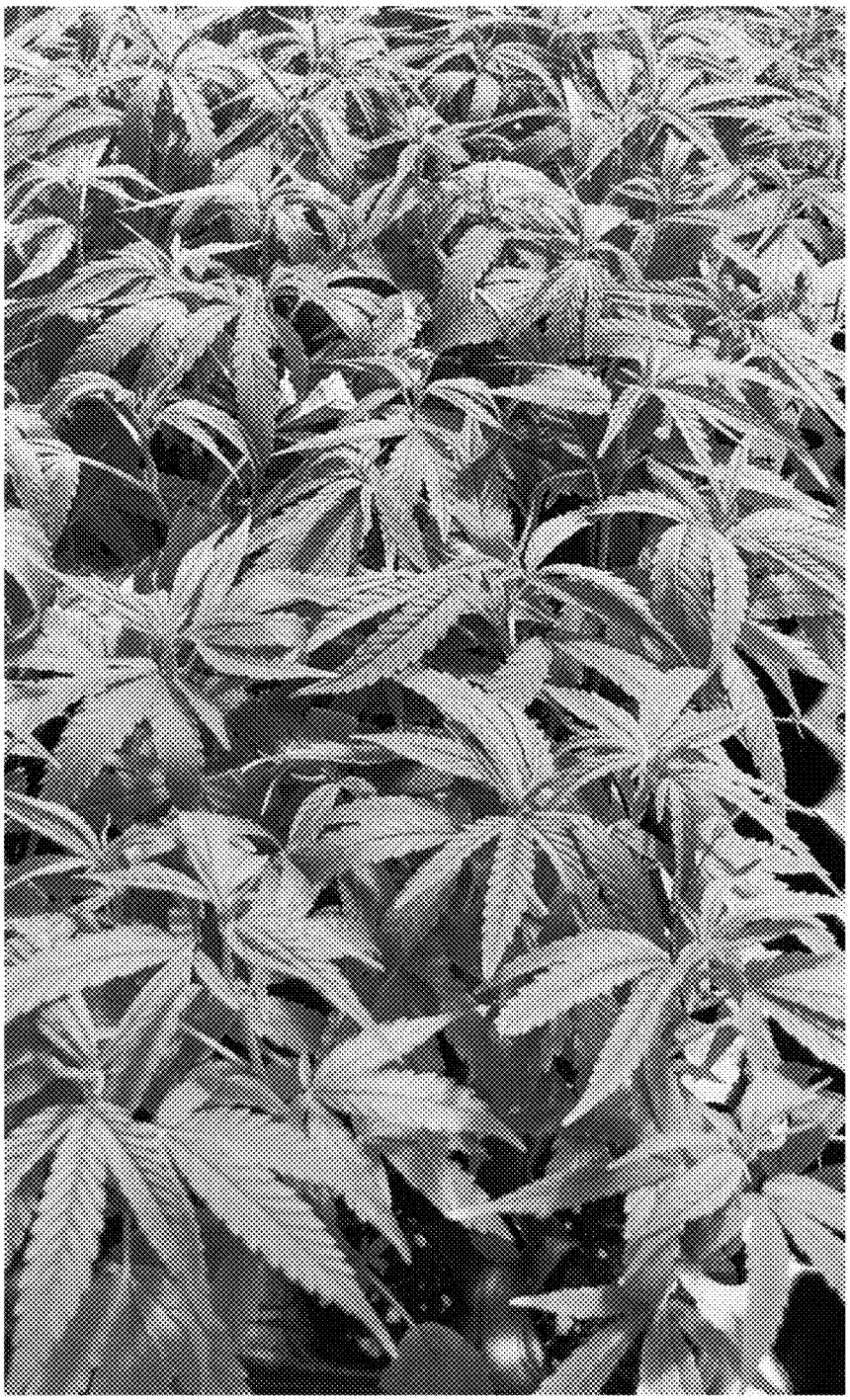
FIG. 6 is a photograph of the cuttings of a plant of 'SW0'.
Figure 7:
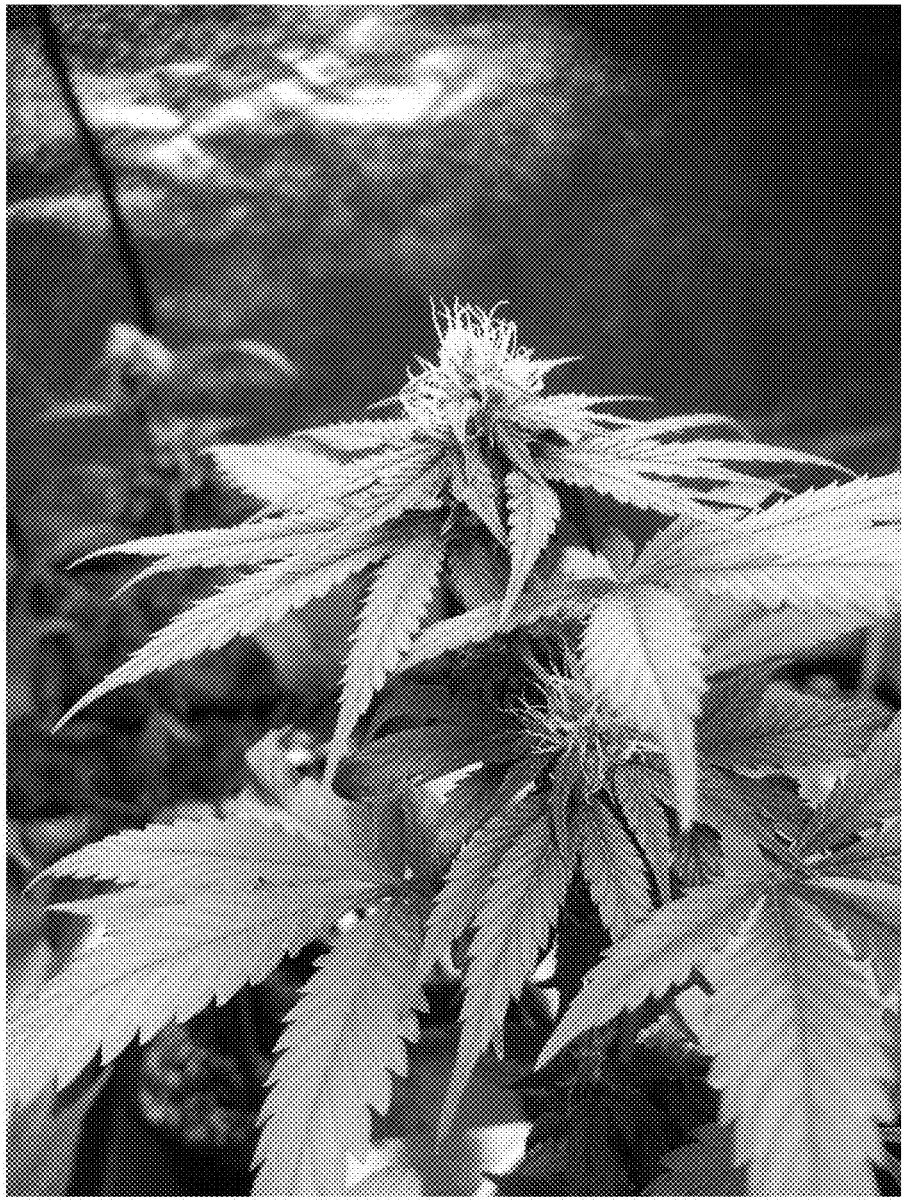
FIG. 7 is a photograph that shows the 5th week of flower of a mature plant of 'SW0'.

Parentage: As depicted in FIG. 1: original parents 'Cherry Wine' x 'The Wife' in reciprocal crosses, followed by sibling crosses and selection to produce 'Superwoman' which was genetically modified to create a THC-null phenotype, designated as 'SW0'.

Market class: Medicinal herb for CBD extraction.

PLANT

General:

a. *Origin*.—Longmont, Colo.
b. *Parentage*.—i. Male parent — 1%. ii. Female parent — 99%.
c. *Average height*.—6-10 feet.
d. *Average spread*.—4-5 feet.
e. *Growth rate*.—Vigorous.
f. *Flower storage life*.—Up to 2 years.
g. *Productivity*.—Up to 5 lbs.
h. *Disease resistance/susceptibility*.—Resistance to powdery mildew, mold.
i. *Pest resistance/susceptibility*.—Resistance to spider mites.

j. *Fragrance*.—A cheesy funk of sweet cherries and garlic pepper.
k. *Proportion of hermaphrodite plants*.—Low.
l. *Proportion of female plants*.—High.
m. *Proportion of male plants*.—Low.
n. *Type of inflorescence*.—Racemose.
o. *Photoperiodicity*.—18 weeks.
p. *Number of flowers per cyme*.—5-7.
q. *Pollen description*.—Medium size pollen sacks.

STEM

General:
a. *Average diameter*.—2-5 inches.
b. *Shape*.—Long, round, and thick.
c. *Average length of internode*.—3-5 inches.
d. *Depth of grooves*.—Medium.
e. *Pith in cross section*.—Medium.
f. *Trichome type*.—Capitate stalked.
g. *Color*.—Green (RGB: 83, 74, 62).

LEAF

General:
a. *Quantity*.—High.
b. *Leaf color*.—Green (RGB 92, 93, 62).
c. *Leaf arrangement*.—5 point tip fan leaf.
d. *Leaf shape*.—Palmate shape.
e. *Leaf margins*.—Serrate.
f. *Undulation of margin*.—No undulation.
g. *Leaf apex shape*.—Sharp.
h. *Leaf base shape*.—Rounded.
i. *Average leaf width*.—5 inches.
j. *Average leaf length*.—9 to 10 inches.
k. *Number of leaflets per leaf*.—5 to 7.
l. *Central leaflet length*.—9 to 10 inches.
m. *Central leaflet width*.—1.5 to 2 inches.
n. *Number of teeth in the middle of leaflet*.—22 teeth.
o. *Margin type*.—Pointy/sharp.
p. *Trichome type* (*top surface*).—Capitate stalked on sugar leaves.
q. *Trichome type* (*bottom surface*).—Capitate stalked.
r. *Texture of top and bottom surfaces*.—Smooth with small ridges on the bottom.
s. *Venation type*.—Pinnately parallel venation.

PETIOLE

General:
a. *Length*.—4 to 5 cm on fan leaves.
b. *Surface texture*.—Smooth.
c. *Anthocyanin intensity*.—Very low.

FEMALE FLOWER

General:
a. *Natural flowering season*.—Second week of August.
b. *Average size*.—1.5 cm per pistil cluster.
c. *Quantity per inflorescence*.—10-14 on apical inflorescence.
d. *General description of calyx*.—Thick with hairs on end of flower.
e. *General description of cola*.—Thick and dense covered in trichomes.
f. *General description of node*.—Multiple levels throughout the plant.
g. *Bract*.—i. Size — 0.6 cm. ii. Quantity — 9 to 12. iii. Shape — Almonds/tear shaped. iv. Trichome type — Capitate stalked. v. Case — None. vi. Texture — Soft and sticky.
h. *Bracteole*.—i. Size — 0.6 cm. ii. Quantity — 2 per bract. iii. Shape — Half drop. iv. Trichome type — Capitate stalked.
i. *Stigma*.—i. Size — 1 inch. ii. Quantity — Dense. iii. Shape — Stringy, long and curly. iv. Trichome type — Capitate stalked.
j. *Stipule*.—i. Size — ¼ inch. ii. Quantity —2 per internode. iii. Shape — Almond with pointy end. iv. Trichome type — Capitate stalked.
k. *Ovary*.—i. Position — Central. ii. Shape — Oval. iii. Length —1 mm.

SEEDS

General:
a. *Shape*.—Oval and uniform shape.
b. *Length*.—3.1 mm.
c. *Width*.—2.3 mm.
d. *Weight per* 1000 *seeds*.—13 grams.
e. *Marbling*.—Strong.
f. *Marbling length*.—1.5-2 mm.
g. *Cotyledon measurements*.—5 mm.

What is claimed is:

1. A new and distinct variety of *Cannabis* plant named 'SW0', as illustrated and described herein.

* * * * *

*Genotypes selected from the segregating population of reciprocal crosses.